US010736838B2

(12) United States Patent
Engqvist et al.

(10) Patent No.: US 10,736,838 B2
(45) Date of Patent: Aug. 11, 2020

(54) TRANSDERMAL DRUG ADMINISTRATION DEVICE

(71) Applicant: EMPLICURE AB, Uppsala (SE)

(72) Inventors: Håkan Engqvist, Uppsala (SE); Susanne Bredenberg, Uppsala (SE); Anders Petterson, Uppsala (SE); Thomas Lundqvist, Uppsala (SE); Anna Dahlgren, Uppsala (SE); Anders Sågström, Uppsala (SE)

(73) Assignee: Emplicure AB, Uppsala (SE)

( * ) Notice: Subject to any disclaimer, the term of this patent is extended or adjusted under 35 U.S.C. 154(b) by 0 days.

(21) Appl. No.: 16/376,317

(22) Filed: Apr. 5, 2019

(65) Prior Publication Data

US 2019/0282494 A1   Sep. 19, 2019

Related U.S. Application Data

(63) Continuation of application No. 13/821,039, filed as application No. PCT/GB2011/051658 on Sep. 5, 2011, now Pat. No. 10,251,834.

(60) Provisional application No. 61/380,539, filed on Sep. 7, 2010.

(51) Int. Cl.
| *A61K 9/14* | (2006.01) |
| *A61K 9/00* | (2006.01) |
| *A61K 31/437* | (2006.01) |
| *A61K 31/445* | (2006.01) |
| *A61K 47/02* | (2006.01) |
| *A61K 47/32* | (2006.01) |
| *A61M 35/00* | (2006.01) |
| *A61K 31/4468* | (2006.01) |
| *A61M 37/00* | (2006.01) |

(52) U.S. Cl.
CPC .......... *A61K 9/0014* (2013.01); *A61K 9/0021* (2013.01); *A61K 31/437* (2013.01); *A61K 31/445* (2013.01); *A61K 31/4468* (2013.01); *A61K 47/02* (2013.01); *A61K 47/32* (2013.01); *A61M 35/00* (2013.01); *A61M 37/0015* (2013.01)

(58) Field of Classification Search
None
See application file for complete search history.

(56) References Cited

U.S. PATENT DOCUMENTS

| 4,861,599 | A | 8/1989 | Springolo et al. |
| 5,318,779 | A | 6/1994 | Hakamatsuka et al. |
| 5,443,812 | A | 8/1995 | Nakajima et al. |
| 5,902,591 | A | 5/1999 | Herstein |
| 6,123,925 | A | 9/2000 | Barry et al. |
| 6,334,856 | B1 | 1/2002 | Allen et al. |
| 6,342,249 | B1 | 1/2002 | Wong et al. |
| 6,503,231 | B1 | 1/2003 | Prausnitz et al. |
| 6,635,281 | B2 | 10/2003 | Wong et al. |
| 6,767,557 | B2 | 7/2004 | Ulrich et al. |
| 8,062,573 | B2 | 11/2011 | Kwon |
| 2002/0122828 | A1 | 9/2002 | Liu |
| 2003/0096002 | A1 | 5/2003 | Borek et al. |
| 2003/0118641 | A1 | 6/2003 | Maloney et al. |
| 2005/0163856 | A1 | 7/2005 | Maloney et al. |
| 2005/0273046 | A1 | 12/2005 | Kwiatkowski et al. |
| 2006/0024358 | A1 | 2/2006 | Santini, Jr. et al. |
| 2006/0057206 | A1 | 3/2006 | Wong et al. |
| 2006/0165787 | A1 | 7/2006 | Moerck et al. |
| 2007/0053986 | A1 | 3/2007 | Kuhn et al. |
| 2007/0123837 | A1 | 5/2007 | Adachi et al. |
| 2007/0151485 | A1 | 7/2007 | Hermansson et al. |
| 2007/0212414 | A1 | 9/2007 | Baichwal et al. |
| 2007/0224129 | A1 | 9/2007 | Guimberteau et al. |
| 2007/0248656 | A1 | 10/2007 | Galer |
| 2007/0292526 | A1 | 12/2007 | Barbe et al. |
| 2008/0063725 | A1 | 3/2008 | Guimberteau et al. |
| 2008/0107720 | A1 | 5/2008 | Walters et al. |
| 2008/0200262 | A1 | 8/2008 | Whity et al. |
| 2008/0214987 | A1 | 9/2008 | Xu |

FOREIGN PATENT DOCUMENTS

| CN | 101104080 A | 1/2008 |
| EA | 010826 A1 | 12/2006 |
| EP | 0 265 061 A1 | 9/1987 |
| EP | 0 336 014 B1 | 6/1992 |
| EP | 0 947 489 B1 | 10/1999 |
| EP | 1 285 655 A1 | 2/2003 |
| EP | 1 674 094 A1 | 6/2006 |
| EP | 2 100 850 A1 | 9/2009 |
| EP | 1429819 | 11/2010 |
| GB | 2 307 862 A | 6/1997 |
| JP | 02-268104 | 11/1990 |
| JP | H-07-188000 | 7/1995 |
| JP | 0930988 | 2/1997 |
| WO | 1989/05632 A1 | 6/1989 |
| WO | 2001/72663 A2 | 10/2001 |
| WO | 2003/090729 A1 | 11/2003 |
| WO | 2003/092785 A1 | 11/2003 |
| WO | 2004/024224 A1 | 3/2004 |
| WO | 2004/028577 A1 | 4/2004 |
| WO | 2004/040036 A1 | 5/2004 |
| WO | 2004/058194 A1 | 7/2004 |

(Continued)

OTHER PUBLICATIONS

CAI et al. "Self-setting bioceramic microscopic protrusions for transdermal drug delivery" Journal of Materials Chemistry B (2014) 2, 5992-5998.

(Continued)

*Primary Examiner* — David J Blanchard
*Assistant Examiner* — Daniel F. Coughlin
(74) *Attorney, Agent, or Firm* — McDonnell Boehnen Hulbert & Berghoff LLP

(57) ABSTRACT

A transdermal drug administration device comprising a drug delivery element (10) defining a contact surface (12) for location, in use, against a patient's skin. The drug delivery element (10) includes a sustained-release pharmaceutical composition. The composition comprises a network of a carrier material having a high mechanical strength and an active pharmaceutical ingredient. The active pharmaceutical ingredient is co-formedly interspersed within pores in the solid, continuous network of the carrier material.

25 Claims, 2 Drawing Sheets

(56) References Cited

FOREIGN PATENT DOCUMENTS

| WO | 2005/037268 A1 | 4/2005 |
|---|---|---|
| WO | 2005/039508 A1 | 5/2005 |
| WO | 2005/065319 A3 | 7/2005 |
| WO | 20050051358 A1 | 9/2005 |
| WO | 20060000229 | 1/2006 |
| WO | 2006/017336 A2 | 2/2006 |
| WO | 2006/089843 A2 | 8/2006 |
| WO | 2006/096544 A1 | 9/2006 |
| WO | 2006/083904 A2 | 10/2006 |
| WO | 2007/074349 A2 | 7/2007 |
| WO | 2008/080109 A1 | 7/2008 |
| WO | 2008/105737 A1 | 9/2008 |
| WO | 2008/105738 A1 | 9/2008 |
| WO | 2008/105739 A1 | 9/2008 |
| WO | 2008/118096 A1 | 10/2008 |
| WO | 2008/142572 A2 | 11/2008 |
| WO | 2009/113856 A1 | 9/2009 |
| WO | 2010/096704 A2 | 8/2010 |

OTHER PUBLICATIONS

Gupta, Manish et al. "Formation of Physically Stable Amorphous Drugs by Milling with Neusilin" Journal of Pharmaceutical Sciences, vol. 92, No. 3, (2003) 536-551.
Wagh, Arun "Chemically Bonded Phosphate Ceramics" Argonne National Laboratories, Elsevier Ltd. Section 1.1 (2004) 1-2.
Figiel, P., et al., "Properties of Alumina Ceramics Obtained by Conventional and Non-conventional Methods for Sintering Ceramics" Journal of Achievements in Materials and Manufaturing Engineering, vol. 48, Issue 1, pp. 29-34, Sep. 2011.
Martindale: The Complete Drug Reference, Analgesics Anti-inflammatory Drugs and Antipyretics, 35th Edition, Pharmaceutical Press, p. 90, 2007.
"Breast Cancer" American Cancer Society, accessed online at www.cancer.org on Jan. 26, 2014, pp. 1-133.
Cai et al., "The effect of curing conditions on compression strength and porosity of metakaoline-based geopolymers" Ceram. Eng. Sci. Proc. (2013), vol. 34, pp. 49-56.
Michelle N. Chretien "Supramolecular photochemistry in zeolites: from catalysts to sunscreens" Pure and Applied Chemistry (2007), vol. 79 (1), pp. 1-20.
De Silva et al., "The role of Al2O3, SiO2 and Na2O on the Amorphous crystalline phase transformation in geopolymer systems" Journal of the Australian Ceramic Society (2009), vol. 45(1), pp. 63-71.
Kawano et al., "Experimental study on the formation of zeolites from obsidian by interaction with NaOH and KOH solutions at 150 and 200° C." Clays and Clay Minerals (1997), vol. 45 (3), pp. 365-377.
Lin et al., "A study of purified montmorillonite intercalated with 5-fluorouracil as drug carrier" Biomaterials 23 (2002), pp. 1981-1987.
Rowe et al., "Handbook of Pharmaceutical Excipients" 2003 4th Edition, pp. 89-92.
Lin, Xian, "Petroleum Engineering Construction" vol. 3 1 No. 5 Serial No. 186 Oct. 2005, Last page is Contents and Abstracts in English.
Bordeepong, Sunaree, et al.; Characterization of halloysite from Thung Yai District, Nakhon Si Thammarat Province, in Southern Thailand; Songklanakarin J. of Sci. Technol. (2011) 33 (5), 599-607.
Duxson, P., et al.; Geopolymer technology: the current state of the art; J. Mater. Sci. (2007) 42:2917-2933.
Cai, B. et al. "Bioceramic microneedles with ftexible and self-swelling substrate" Eu. J. Pharm. Biopharm., 94 (2015) 404-410.
Cai, B., et al. "Development and evaluation of a tampering resistant transdermal fentanyl patch" Int. J. of Pharm. vol. 488 (2015) 102-107.
Gbureck, U., et al.; Low temperature direct 3D printed bioceramics and biocomposites as drug release matrices; J. of Controlled Release 122 (2007) 173-180; Science Direct.
Mostafa, N.Y., Characterization, thermal stability and sintering of hydroxyapatite powders prepared by different routes; Mater. Chem. Phys. 2005, 94, 333-341.
Petermann, J., et al., Alkali-Activated Geopolymers: A Literature Review; Air Force Research Laboratory, Jul. 2010.
Price, R.R., et al., In-vitro release characteristics of tetracycline HC1, khellin and nicotinamide adenine dineculeotide from halloysite; a cylindrical mineral; Microencapsulation; 2001; vol. 18, No. 6, 713-722.
Steveson, M. et al., Relationships between composition, structure and strength of inorganic polymers; J. of Materials Science 40 (2005) 2023-2036.
"Halloysite and Kaolinite," The James Hutton Institute, available at <http://www.claysandminerals.com/materials/halloysite>, as accessed Jul. 14, 2014.
Banga et al., "Microporation applications for enhancing d4ug delivery" Expert Opinion Drug Delivery (2009), vol. 6, pp. 343-354.
Byrne et al., "Use of porous aluminosilicate pellets for drug delivery" Journal of Micoroencapsulation (2005), vol. 22(4), pp. 423-437.
DURAGESIS® Information Sheet, Janssen Pharmaceuticals, Inc. (2009).
Forsgren et al., "A ceramic drug delivery vehicle for oral administration of highly potent opioids" Journal of Pharmaceutical Sciences (2010), vol. 99(1), pp. 219-226.
Jamstorp et al., "Mechanically strong geopolymers offer new possibilities in treatment of chronic pain" Journal of Controlled Release (2010), vol. 146, pp. 370-377.
Lassere et al., "Ceramic drug-delivery devices" Critical Reviews in Therapeutic Drug Carrier Systems (1998), vol. 15, pp. 1-56.
Levis et al., "Use of coated microtubular halloysite for the sustained release of diltiazem hydrochloride and propranolol hydrochloride" International Journal of Pharmaceutics (2003), vol. 253, pp. 145-157.
Rimoli et al., Synthetic zeolites as a new tool for drug delivery Journal of Biomedical Materials Research (2008), vol. 87(A) pp. 156-164.
Zheng et al., "Preparation of geopolymer precursors by sol-gel method and their characterization" J. Materials Science (2009), vol. 44, pp. 391-3996.
Zoulgami et al., "Synthesis and physico-chemical characterization of a polysialate-hydroxyapatite composite for potential biomedical application" The European Physical Journal Applied Physics (2002), vol. 19, pp. 173-179.
Michael E. Aulton, "Dosage form design and manufacuture" Aulton's Pharmaceutics, (2010),Third Edition, pp. 4-7 and 483-485.
Byrne et al., "Use of commercial porous ceramic particles for sustained drug delivery" International Journal of Pharmaceutics (2002), vol. 246, pp. 61-73.
Cavallaro et al., "Drug delivery devices based on mesoporous silicate" Drug Delivery (2004), vol. 11, pp. 41-46.
Joseph Davidovits "30 years of successes and failures in Geopolymer Applications Market trends and potential breakthroughs" Geopolymer 2002 Conferences (2002), pp. 1-16.
Duxson et al., "Geopolymer technology: the current state of the art" Journal Material Science (2007), vol. 42, pp. 2917-2933.
Itokazu et al., "Development of porous apatite ceramic for local delivery of chemotherapeutic agents" J. Biomed. Material Res. (1998), vol. 39, pp. 536-538.
Komlev et al., Porous hydroxyapatite ceramics of bi-modal pore size distribution Journal of Materials Science (2002), vol. 13, pp. 295-299.
Krajewski et al., "Porous ceramic bodies for drug delivery" Journal of Materials Science (2000), vol. 12, pp. 763-771.
Medvecky et al., "Study of controlled tetracycline release from porous calcium phosphate/polyhydroxybutyrate composites" Chemical Papers (2007), vol. 61, pp. 477-484.

(56) References Cited

OTHER PUBLICATIONS

Netz et al., "Potential use of gelcasting hydroxyapatite porous ceramic as an implantable drug delivery system" International Journal of Pharmaceutics (2001), vol. 213, pp. 117-125.
Paul et al., "Tricalcium phosphate delayed release formulation for oral delivery of insulin: A proof-of-concept study" Journal of Pharmaceutical Sciences (2008), vol. 97(2), pp. 875-882.
Rowe et al., "handbook of Pharmaceutical Excipients" Sixth Edition (2009), pp. 525-533 and 581-585.
Yao et al., "Fabrication of hydroxyapatite ceramics with controlled pore characteristics by slip casting" Journal of Materials Science: Material in Medicine (2005), vol. 16, pp. 161-165.

TRANSDERMAL DRUG ADMINISTRATION DEVICE

This application is a continuation of U.S. application Ser. No. 13/821,039, filed Mar. 6, 2013, which is a U.S. national phase of International Application No. PCT/GB2011/051658, filed Sep. 5, 2011, which claims priority to U.S. Provisional Application No. 61/380,539, filed Sep. 7, 2010, the disclosure of each of which is hereby incorporated by reference in its entirety.

FIELD OF THE INVENTION

The invention relates to a new transdermal drug administration device including a non-abusable pharmaceutical composition that provides for the controlled release of active ingredients, such as opioid analgesics, for transdermal administration.

BACKGROUND

The listing or discussion of an apparently prior-published document in this specification should not necessarily be taken as an acknowledgement that the document is part of the state of the art or common general knowledge.

Opioids are widely used in medicine as analgesics, for example in the treatment of patients with severe pain, chronic pain or to manage pain after surgery. Indeed, it is presently accepted that, in the palliation of more severe pain, no more effective therapeutic agents exist.

The term "opioid" is typically used to describe a drug that activates opioid receptors, which are found in the brain, the spinal chord and the gut. Three classes of opioids exist:
(a) naturally-occurring opium alkaloids. These include morphine and codeine;
(b) compounds that are similar in their chemical structure to the naturally occurring alkaloids. These so-called semi-synthetics are produced by chemical modification of the latter and include the likes of diamorphine (heroin), oxycodone and hydrocodone; and
(c) truly synthetic compounds such as fentanyl and methadone. Such compounds may be completely different in terms of their chemical structures to the naturally-occurring compounds.

Of the three major classes of opioid receptors ($\mu$, $\kappa$ and $\delta$), opioids' analgesic and sedative properties mainly derives from agonism at the $\mu$ receptor.

Opioid analgesics are used to treat severe, chronic cancer pain, often in combination with non-steroid anti-inflammatory drugs (NSAIDs), as well as acute pain (e.g. during recovery from surgery and breakthrough pain). Further, their use is increasing in the management of chronic, non-malignant pain.

Optimal management of chronic pain requires around-the-clock coverage. In this respect, opioid-requiring cancer patients are usually given slow-release opioids (slow-release morphine, oxycodone or ketobemidone, or transdermal fentanyl or buprenorphine). Pharmaceutical formulations that are capable of providing a sustained release of active ingredients allow the patient to obtain this baseline analgesia with a minimal number of doses per day. This in turn improves patient compliance and minimizes interference with the individual's lifestyle and therefore quality of life.

Transdermal fentanyl drug delivery systems comprise patches (e.g. DURAGESIC®) that are applied to the skin to deliver that potent opioid analgesic, which is slowly absorbed through the skin into the systemic circulation. Pain may be relieved for up to 3 days from a single patch application. Transdermal buprenorphine patches (e.g. BUTRANS®) relieve pain for up to 7 days after a single patch administration.

In the design of sustained release formulations with extremely potent drugs, such as opioids, the risk for "dose dumping" has to be eliminated in view of the risk of severe and, on occasions, lethal side effects. Secondly, in some instances, patients may misuse their opioid medication, e.g. by willfully (and sometimes unintentionally) tampering with an extended release formulation in order to get more immediate absorption of opioid and a more rapid pain relieving effect. Thirdly, a perennial problem with potent opioid analgesics such as fentanyl is one of abuse by drug addicts. Addicts often apply innovative techniques in their abuse of pharmaceutical formulations, for example by way of one or more of the following processes:
(a) extracting a large quantity of active ingredient from that formulation using an appropriate eluent, such as an acid and/or alcohol, to form a solution, which is then injected intravenously. With most commercially-available pharmaceutical formulations, this can be done relatively easily, which renders them unsafe or "abusable";
(b) heating (and then smoking);
(c) crushing of tablet (and then snorting); and/or
(d) in the case of a patch, making a tea (and then drinking).

Thus, there is a clear unmet clinical need for an effective pharmaceutical formulation that is capable of treating e.g. severe pain via a sustained release of active ingredients (such as opioid analgesics), whilst at the same time minimising the possibility of dose dumping, misuse by opioid treated patients and/or abuse by addicts.

One solution to these problems that has been suggested is the incorporation of the active substance into a polymer matrix (see e.g. US2003/0118641 and US2005/0163856), which allows for the slow release of the active substance. However, this solution is not adequate as the drug abuser could either liberate the active substance from the polymer matrix by co-mixing with a solvent (either prior to ingestion, or the solvent may be co-ingested with the polymer matrix/active substance) or by crushing the polymer matrix.

Ceramics are becoming increasingly useful to the medical world, in view of the fact they are durable and stable enough to withstand the corrosive effect of body fluids.

For example, surgeons use bioceramic materials for repair and replacement of human hips, knees, and other body parts. Ceramics also are being used to replace diseased heart valves. When used in the human body as implants or even as coatings to metal replacements, ceramic materials can stimulate bone growth, promote tissue formation and provide protection from the immune system. Dental applications include the use of ceramics for tooth replacement implants and braces.

Ceramics are also known to be of potential use as fillers or carriers in controlled-release pharmaceutical formulations. See, for example, EP 947 489 A, U.S. Pat. No. 5,318,779, WO 2008/118096, Lasserre and Bajpai, *Critical Reviews in Therapeutic Drug Carrier Systems*, 15, 1 (1998), Byrne and Deasy, *Journal of Microencapsulation*, 22, 423 (2005) and Levis and Deasy, *Int. J. Pharm.*, 253, 145 (2003).

In particular, Rimoli et al, *J. Biomed. Mater. Res.*, 87A, 156 (2008), US patent application 2006/0165787 and international patent applications WO 2006/096544, WO 2006/017336 and WO 2008/142572 all disclose various ceramic substances for controlled release of active ingredients, with the latter two documents being directed in whole or in part to opioid analgesics, with the abuse-resistance being imparted by the ceramic structures' mechanical strength.

Methods employed in these documents typically involve the incorporation of active ingredients into pre-formed porous ceramic materials comprising e.g. porous halloysite, kaolin, titanium oxide, zirconium oxide, scandium oxide, cerium oxide and yttrium oxide. In this respect, loading of active ingredient typically comprises soaking, extrusion-spheronization and/or cryopelletization. It is known to be difficult to infuse drug into a pre-formed porous ceramic structure. Indeed, in the case of opioids, it is considered that such active ingredient-incorporation methodology will not enable the loading of sufficient active ingredient to provide appropriate doses for effective therapeutic pain management, over a prolonged time, given that infusion of active ingredient into preformed pores is a difficult thing to do.

In WO 2008/142572, drugs are incorporated during the formation of a ceramic carrier using chemically bonded ceramics, such as calcium aluminate or calcium silicate. Although this leads to a higher amount of drug incorporation than is typically the case for preformed ceramic materials, the mechanical strength and the chemical stability of the ceramic structures described in WO 2008/142572 is, relatively speaking, limited, especially in acidic conditions. See also Forsgren et al, *J. Pharm. Sci.*, 99, 219 (2010) and Jämstorp et al, *J. Control. Release* (2010) in press.

A composite material having a beneficial agent associated with at least a portion of a high surface area component so as to increase the bioavailability and/or activity of the beneficial agent is disclosed in WO 02/13787. The high surface area component may be formed from a material having a hardness that is greater than the hardness of the beneficial agent, and may be formed from metal oxides, metal nitrides, metal carbides, metal phosphates, carbonaceous materials, ceramic materials and mixtures thereof. The beneficial agent may be associated with the high surface area component by means of spraying, brushing, rolling, dip coating, powder coating, misting and/or chemical vapour deposition.

Various methods of enhancing drug delivery by transdermal administration are described by Banga in *Expert Opin. Drug Deliv.*, 6, 343 (2009), including direct coating onto microneedles and administration via hollow microneedles. See also international patent application WO 03/090729 and WO 2009/113856, U.S. Pat. No. 6,334,856 and US patent application No. US 2009/0200262.

An interface for a transdermal drug administration device is disclosed in US 2007/0123837. The interface may be provided in the form of a flat plate including two-dimensionally arranged projections, capable of piercing the skin, and a plurality of openings, capable of delivering a drug, respectively arranged in correspondence with the projections. The projections may be conical or pyramidal in shape and the flat plate and projections may be formed from a metal, an alloy or a ceramic. In use, in a transdermal drug administration device for example, a drug in liquid form may be held in a drug-containing layer above the flat plate. When the flat plate is pressed against the skin, the plurality of projections pierce the skin and the drug is transferred from the drug-containing layer, via the plurality of openings provided in correspondence with the projections, through the holes formed in the skin.

A device for delivering bioactive agents through the skin is also disclosed in WO 03/092785. The device includes a plurality of skin-piercing members and a porous calcium phosphate coating adapted as a carrier and provided on at least part of the skin-piercing members. The coating includes at least one bioactive agent and the skin-piercing members may be formed from metals, ceramics, plastics, semiconductors or composite materials.

Each of these documents refers to the possibility of loading and/or combining an active ingredient with a preformed delivery device or other carrier, either by means of a separate drug-containing layer provided in combination with the device or a coating applied to the device.

Disclosure of the Invention

According to the invention there is provided a transdermal drug administration device comprising a drug delivery element defining a contact surface for location, in use, against a patient's skin, the drug delivery element including a sustained-release pharmaceutical composition comprising an active pharmaceutical ingredient co-formedly interspersed (dispersed) within pores of a solid, continuous network comprising a carrier material for the active pharmaceutical ingredient and possessing a high mechanical strength.

The term "sustained-release" is employed herein synonymously with the term "controlled-release", and will be understood by the skilled person to include compositions that provide, and/or are adapted to provide, for a "sustained", a "prolonged" and/or an "extended" release of drug (in which drug is released at a sufficiently retarded rate to produce a therapeutic response over a required period of time).

We have advantageously found that the compositions used in the invention provide for release of active ingredient that is substantially uniform and/or nearly constant over an extended period of time. In one embodiment, a nearly constant rate of release can vary over a dose interval from about 30 minutes (e.g. about 6 to about 12 hours) to about (e.g. about 7, for example about 5, such as about 3) days. Constant release may further be defined as a composition being capable of maintaining a steady state concentration in a body fluid not deviating more than about 20% (e.g. about 10%) from the mean value during the dose interval.

The network of the sustained release pharmaceutical composition may either be formed directly from a material that inherently possesses a high mechanical strength or may be formed as a consequence of a chemical reaction between one or more precursor substances or materials, so forming the three-dimensional network in situ. In this respect, the network may be designed to be inert in the following ways:

(a) general physico-chemical stability under normal storage conditions, including temperatures of between about minus 80 and about plus 50° C. (preferably between about 0 and about 40° C. and more preferably room temperatures, such as about 15 to about 30° C.), pressures of between about 0.1 and about 2 bars (preferably at atmospheric pressure), relative humidities of between about 5 and about 95% (preferably about 10 to about 75%), and/or exposure to about 460 lux of UV/visible light, for prolonged periods (i.e. greater than or equal to six months). Under such conditions, carrier material networks as described herein may be found to be less than about 5%, such as less than about 1% chemically degraded/decomposed, as above;

(b) particularly importantly when the active ingredient that is employed is an opioid analgesic, general physico-chemical stability under acidic, alkaline and/or alcoholic (e.g. ethanolic) conditions at room temperature and/or under at elevated temperatures (e.g. up to about 200° C.), which may result in less than about 15% degradation, so avoiding the possibility of deliberate ex vivo extraction of drug for intended abuse (e.g. by acid or alcohol extraction, followed by injection, or heating a composition of the invention and then an opioid addict inhaling the vapour or smoke that is given off); and (c) again, particularly importantly when the active ingredient that is employed is an opioid analgesic, general physical stability, for example with a high mechanical impact strength, so reducing the possibility of mechanical grinding or milling with a view to extraction of active ingredient as defined in (b) above, or by an opioid addict sniffing a resultant powder directly.

With reference to (c) above, it is preferred in this respect that the network exhibits a compressive strength of greater than about 1 MPa, such as greater than about 5 MPa, e.g. about 10 MPa on micro- and nano-structure level, which is high enough to withstand breakdown of the material at the microstructure level, i.e. of less than about 200 µm.

In this respect, by network of "high mechanical strength" we also include that the structure of that network maintains its overall integrity (e.g. shape, size, porosity, etc) when a force of about 1 kg-force/cm$^2$ (9 newtons/cm$^2$), such as about 5 kg-force/cm$^2$ (45 newtons/cm$^2$), such as about 7.5 kg-force/cm$^2$, e.g. about 10.0 kg-force/cm$^2$, preferably about 15 kg-force/cm$^2$, more preferably about 20 kg-force/cm$^2$, for example about 50 kg-force/cm$^2$, especially about 100 kg-force/cm$^2$ or even about 125 kg-force/cm$^2$ (1125 newtons/cm$^2$) is applied using routine mechanical strength testing techniques known to the skilled person (for example using a so-called "compression test" or "diametral compression test", employing a suitable instrument, such as that produced by Instron (the "Instron Test", in which a specimen is compressed, deformation at various loads is recorded, compressive stress and strain are calculated and plotted as a stress-strain diagram which is used to determine elastic limit, proportional limit, yield point, yield strength and (for some materials) compressive strength)). When the structure of the network is particulate, at least about 40% (e.g. at least about 50%, such as at least about 60% preferably, at least about 75%, and more preferably at least about 90%) of the particles (whether primary or secondary particles) maintain their integrity under these conditions.

The carrier material that forms the solid, continuous network of the composition is preferably inorganic, but may also comprise an inert plastics or polymeric material, such as a polyacrylate or a copolymer thereof, a polyethylene glycol, a polyethylene oxide, a polyethylene, a polypropylene, a polyvinyl chlorides, a polycarbonate, a polystyrene, a polymethylmethacrylate, and the like.

In certain embodiments of the invention, the carrier material may be based on one or more ceramic materials.

The term "ceramic" will be understood to include compounds formed between metallic and nonmetallic elements, frequently oxides, nitrides and carbides that are formed and/or processable by some form of curing process, which often includes the action of heat. In this respect, clay materials, cement and glasses are included within the definition of ceramics (Callister, "*Material Science and Engineering, An Introduction*" John Wiley & Sons, 7$^{th}$ edition (2007)).

It is preferred that the ceramic material that is employed is based upon an aluminate, such as a calcium aluminate or, more preferably, a silicate such as an aluminium (alumino) silicate. However, it may also be an oxide and/or a double oxide, and/or a nitride and/or a carbide of any of the elements silicon, aluminium, carbon, boron, titanium, zirconium, tantalum, scandium, cerium, yttrium or combinations thereof.

Preferred materials include aluminium silicate and/or aluminium silicate hydrate (crystalline or amorphous). Non-limiting examples include kaolin, dickite, halloysite, nacrite, ceolite, illite or combinations thereof, preferably halloysite. The grain size of the ceramic material (e.g. aluminium silicate) may be below about 500 µm, preferably below about 100 µm, and particularly below about 20 µm, as measured by laser diffraction in the volume average mode (e.g. Malvern master size). The grains may be of any shape (e.g. spherical, rounded, needle, plates, etc.).

Ceramics may comprise chemically bonded ceramics (non-hydrated, partly hydrated or fully hydrated ceramics, or combinations thereof). Non-limiting examples of chemically bonded ceramics systems include calcium phosphate, calcium sulphates, calcium carbonates, calcium silicates and calcium aluminates. Preferred chemical compositions include those based on chemically bonded ceramics, which following hydration of one or more appropriate precursor substances consume a controlled amount of water to form a network of high mechanical strength. The preferred systems available are those based on aluminates and silicates, both of which consume a great amount of water. Phases such CA2, CA, CA3 and C12A7, and C2S and C3S in crystalline or amorphous state (C=CaO, A=Al$_2$O$_3$, SiO$_2$=S, according to common cement terminology) may be used, which are readily available. The calcium aluminate and/or calcium silicate phases may be used as separate phase or as mixtures of phases. The above-mentioned phases, all in non-hydrated form, act as the binder phase (the cement) in the carrier material when hydrated.

The mean grain size of any ceramic precursor powder particles may be below about 100 µm, preferably between about 1 µm and about 20 µm. This is to enhance hydration. Such precursor material may be transformed into a nano-size microstructure during hydration. This reaction involves dissolution of the precursor material and repeated subsequent precipitation of nano-size hydrates in the water (solution) and upon remaining non-hydrated precursor material. This reaction favourably continues until precursor materials have been transformed and/or until a pre-selected porosity determined by partial hydration using the time and temperature, as well as the H$_2$O in liquid and/or humidity, is measured.

In other (e.g. preferred) embodiments of the invention, the carrier material of the network of the composition may be based on one or more geopolymer materials.

The term "geopolymer" will be understood by those skilled in the art to include or mean any material selected from the class of synthetic or natural aluminosilicate materials which may be formed by reaction of an aluminosilicate precursor substance (preferably in the form of a powder) with an aqueous alkaline liquid (e.g. solution), preferably in the presence of a source of silica.

The term "source of silica" will be understood to include any form of a silicon oxide, such as SiO$_2$, including a silicate. The skilled person will appreciate that silica may be manufactured in several forms, including glass, crystal, gel, aerogel, fumed silica (or pyrogenic silica) and colloidal silica (e.g. Aerosil).

Suitable aluminosilicate precursor substances are typically (but not necessarily) crystalline in their nature include kaolin, dickite, halloysite, nacrite, zeolites, illite, preferably dehydroxylated zeolite, halloysite or kaolin and, more preferably, metakaolin (i.e. dehydroxylated kaolin). Dehydroxylation (of e.g. kaolin) is preferably performed by calcining (i.e. heating) of hydroxylated aluminosilicate at temperatures above 400° C. For example, metakaolin may be prepared as described by Stevenson and Sagoe-Crentsil in *J. Mater. Sci.*, 40, 2023 (2005) and Zoulgami et al in *Eur. Phys J. AP*, 19, 173 (2002), and/or as described hereinafter. Dehydroxylated aluminosilicate may also be manufactured by condensation of a source of silica and a vapour comprising a source of alumina (e.g. $Al_2O_3$).

Precursor substances may also be manufactured using sol-gel methods, typically leading to nanometer sized amorphous powder (or partly crystalline) precursors of aluminosilicate, as described in Zheng et al in *J. Materials Science*, 44, 3991-3996 (2009). This results in a finer microstructure of the hardened material. (Such as sol-gel route may also be used in the manufacture of precursor substances for the chemically bonded ceramic materials hereinbefore described.)

If provided in the form of a powder, the mean grain size of the aluminosilicate precursor particles are below about 500 μm, preferably below about 100 μm, more preferred below about 30 μm.

In the formation of geopolymer materials, such precursor substances may be dissolved in an aqueous alkaline solution, for example with a pH value of at least about 12, such as at least about 13. Suitable sources of hydroxide ions include strong inorganic bases, such as alkali or alkaline earth metal (e.g. Ba, Mg or, more preferably, Ca or, especially Na or K, or combinations thereof) hydroxides (e.g. sodium hydroxide). The molar ratio of metal cation to water can vary between about 1:100 and about 10:1, preferably between about 1:20 and about 1:2.

A source of silica (e.g. a silicate, such as $SiO_2$) is preferably added to the reaction mixture by some means. For example, the aqueous alkaline liquid may comprise $SiO_2$, forming what is often referred to as waterglass, i.e. a sodium silicate solution. In such instances, the amount of $SiO_2$ to water in the liquid is preferably up to about 2:1, more preferably up to about 1:1, and most preferably up to about 1:2. The aqueous liquid may also optionally contain sodium aluminate.

Silicate (and/or alumina) may alternatively be added to the optionally powdered aluminosilicate precursor, preferably as fume silica (microsilica; AEROSIL® silica). The amount that may be added is preferably up to about 30 wt %, more preferably up to about 5 wt. % of the aluminosilicate precursor.

The presence of free hydroxide ions in this intermediate alkaline mixture, causes aluminium and silicon atoms from the source material(s) to be dissolved. The geopolymer materials may then be formed by allowing the resultant mixture to set (cure or harden), during which process the aluminium and silicon atoms from the source materials reorientate to form a hard (and at least largely) amorphous geopolymeric material. Curing may be performed at room temperature, at elevated temperature or at reduced temperature, for example at around or just above ambient temperature (e.g. between about 20° C. and about 90° C., such as around 40° C.). The hardening may also be performed in any atmosphere, humidity or pressure (e.g. under vacuum or otherwise). The resultant inorganic polymer network is in general a highly-coordinated 3-dimensional aluminosilicate gel, with the negative charges on tetrahedral $Al^{3+}$ sites charge-balanced by alkali metal cations.

In this respect, a geopolymer-based carrier material may be formed by mixing a powder comprising the aluminosilicate precursor and an aqueous liquid (e.g. solution) comprising water, a source of hydroxide ions as described hereinbefore and the source of silica (e.g. silicate), to form a paste. The ratio of the liquid to the powder is preferably between about 0.2 and about 20 (w/w), more preferably between about 0.3 and about 10 (w/w). Calcium silicate and calcium aluminate may also be added to the aluminosilicate precursor component.

For the avoidance of doubt, whatever the network of carrier material that forms part of the sustained release pharmaceutical composition comprises, or is composed of, it is necessary to provide the active pharmaceutical ingredient together with either:

(a) particulate, pre-formed ceramic, geopolymeric or polymeric material; or
(b) some sort of "precursor" to the ceramic, geopolymeric or polymeric material, for example in the form of a paste, and then perform some sort of appropriate (e.g. curing or bonding) process, which comprises either:

(i) bonding together (physically or chemically) the particles (a); or
(ii) in the case of (b), a chemical reaction, to form, in both cases, the solid, continuous, three-dimensional network with a high mechanical strength.

In accordance with the invention, the active pharmaceutical ingredient is co-formedly interspersed in pores within the carrier material network. This means that, whatever process is employed to form the solid, continuous, three-dimensional network with high mechanical strength, it must also necessarily form pores within which active pharmaceutical ingredient is interspersed.

The active ingredient may thus be mixed with the carrier material (e.g. ceramic or geopolymer) or precursor(s) thereto, by way of a variety of techniques, such as introduction by way of a sol-gel process, as a solution, or as a slurry, a paste or a putty of, for example, particles, granules or pellets of carrier material or precursor(s) thereto, in the presence of an appropriate liquid (e.g. an aqueous or organic solvent). This is followed by some sort of "curing" process to form the sustained release composition, which comprises said pores, within which the active ingredient resides.

Such pores are themselves a three-dimensional network of channels or voids within the solid network, containing (e.g. particles) of active ingredient, and are thus to be distinguished from pre- or post-formed channels (in, for example, microneedles) through which drug is administered to or through the skin in the form of a pharmaceutical compositions (e.g. a solution).

Such pores may thus be essentially "secondary pores" formed by chemical interactions (e.g. "bonding") between the surfaces of primary particles of (e.g. inorganic) materials of high mechanical strength (which may be porous in their own right (i.e. comprise "primary" pores), such as ceramics or geopolymers. Such pores may, for example, result from exposure of such materials to one or more chemical reagents that cause a physical and/or chemical transformation (such as a partial dissolution) at, and subsequent physical and/or chemical bonding together of, those surfaces (which may in itself result as a consequence of some other physico-chemical process such as drying, curing, etc.), giving rise to said pores/voids.

In such instances, such chemical reagents may be mixed together with active pharmaceutical ingredient during preparation of the sustained release composition. However, such secondary pores are not necessarily formed in this way, and bonding together of primary particles of carrier materials may also be physical and/or mechanical.

Thus, in such embodiments of the invention, a sustained-release pharmaceutical composition is provided, comprising a solid, continuous three-dimensional network comprising particles of a (preferably inorganic) carrier material, which particles are bonded together to form secondary pores or voids, and an active ingredient interspersed within said voids.

Alternatively, if the network is formed by way of a chemical reaction (e.g. polymerisation, or as described hereinbefore for geopolymers), active ingredient may be co-mixed with a precursor mixture comprising relevant reactants and thereafter located within pores or voids that are formed during formation of the three-dimensional carrier material network itself. Although it is not essential in all cases, it may be that, in some cases, it is necessary to include a porogenic material as part of the reaction mixture in order to assist in the formation of pores within the final carrier material network, within which active pharmaceutical ingredient is co-formedly interspersed. Porogenic materials include, for example, oils, liquids (e.g. water), sugars, mannitol etc.

The composition may further include a film forming agent co-formedly interspersed within the pores of the network.

When used herein, the term "film-forming agent" refers to a substance that is capable of forming a film over (or within), or coating over, another substance or surface (which may be in particulate form).

The use of a film forming agent improves the tamper resistance of the transdermal drug administration device and may also further advantageously increase the mechanical strength of the composition. These features, together with the controlled-release properties of the composition, provide advantages associated with the prevention of dose dumping and potential misuse or drug abuse by ex vivo extraction of the active pharmaceutical ingredient, when the latter comprises an opioid analgesic or other compound with a risk of misuse/abuse.

It is preferred that any such film-forming agent is a material that is capable of providing a sustained-release, delayed-release or, preferably, enteric-release coating (i.e. an enteric coating material). Substances that are capable of providing an enteric coating are thus those that may be employed in peroral pharmaceutical formulations as a barrier to prevent or minimise release of active ingredient prior to such formulations reaching the small intestine.

In this respect, it is preferred that the film-forming agent is a polymer. Examples of polymers that may be employed as film-forming agents include, without limitation: alkylcellulose polymers (e.g. ethylcellulose polymers), and acrylic polymers (e.g. acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamid copolymer, poly(methyl methacryate), poly (methacrylic acid) (anhydride), methyl methacrylate, polymethacrylate, methyl methacrylate copolymer, poly(m-ethyl methacrylate), poly(methyl methacrylate) copolymer, polyacryamide, aminoalkyl methacrylate copolymer, poly (methacrylic acid anhydride), and glycidyl methacrylate copolymers). The polymer may also be a mixture of polymers. Typically, the molecular weight (weight average and/ or number average) of the polymer is 1,000 to 10,000,000, 10,000 to 1,000,000, preferably 50,000 to 500,000 g/mol, as measured by gel permeation chromatography.

Preferred polymers include the alkyl cellulose polymers and acrylic polymers described herein.

The film-forming agent may comprise a polymer that exhibits anionic character and/or is weakly acidic (for example that have or provide a pH of less than 7, and preferably less than 5, in an aqueous medium).

Most preferred polymers includes those derived from methacrylic acid and ethyl acrylate (preferably in a 1:1 ratio), or neutral methacrylic polymers with acid or alkaline groups, including those marketed under the trademarks Kollicoat® and Eudragit®. For example, Kollicoat® MAE 30 DP (BASF) is a copolymer of methacrylic acid/ethyl acrylate (1:1), and is available as an aqueous dispersion or powder. Other polymers that may be mentioned include Eudragit® L100-55.

In embodiments in which a film-forming agent is included in the composition, the admixing of active ingredient and film-forming agent may take place prior to or during interspersion within the network of carrier material, such that the majority (i.e. greater than about 50%, such as greater than about 75%) of those components are added to the carrier material or precursor(s) thereto at essentially the same time, and not separately, such that there is substantially uniform blending/inter-mixing of the components as defined above. Most preferably, there is a substantially uniform content (i.e. variations of no more than about ±50%, such as about ±40%, preferably about ±30%, more preferably about ±20% and particularly about ±10%) of the active ingredient throughout the film-forming agent, and/or there is no particular location within the film-forming agent where there is a substantially greater concentration of the active ingredient to provide a homogeneous distribution.

The composition may further comprise one or more commonly-employed pharmaceutical excipients. Suitable excipients include inactive substances that are typically used as a carrier for the active pharmaceutical ingredients in medications. Suitable excipients also include those that are employed in the pharmaceutical arts to bulk up drug delivery systems that employ very potent active pharmaceutical ingredients, to allow for convenient and accurate dosing. Alternatively, excipients may also be employed to aid in the handling of the active pharmaceutical ingredient concerned.

In this respect, pharmaceutically-acceptable excipients include filler particles, by which we include particles that do not take part in any chemical reaction during which a composition is formed. Such filler particles may be added as ballast and/or may provide the composition with functionality.

The composition may also optionally contain bulking agents, porogens, pH modifiers, dispersion agents or gelating agents to control the rheology or the amount of liquid in the geopolymer. The total amount of such excipients is limited to about 20 wt % of the total weight of the precursor and liquid combined. Non-limiting examples of such excipients include polycarboxylic acids, cellulose, polyvinylalcohol, polyvinylpyrrolidone, starch, nitrilotriacetic acid (NTA), polyacrylic acids, PEG, glycerol, sorbitol, mannitol and combinations thereof.

Additional pharmaceutically-acceptable excipients include carbohydrates and inorganic salts such as sodium chloride, calcium phosphates, calcium carbonate, calcium silicate and calcium aluminate. In the case of networks based on geopolymers, such additional materials are preferably added to the aluminosilicate precursor component.

As defined herein, the drug delivery element defines a contact surface for location, in use, against a patient's skin and includes the sustained-release pharmaceutical composition comprising the carrier material network and active pharmaceutical ingredient. Accordingly, it is not essential that the sustained-release pharmaceutical composition is placed in direct contact with the skin. Indeed, the composition may be coated with a coating material (e.g. a thin, porous film or hydrophilic or hydrophobic chemical substances, such as surface active molecules, e.g. silicones or fluoroalkyl materials).

The drug delivery element of the drug delivery device according to the invention may take several forms, provided that it defines a contact surface for location, in use, against a patient's skin.

For example, the composition may be incorporated into the drug delivery element of the transdermal drug administration device in the form of pellets or particles of the composition. In such embodiments, the pellets may be embedded in any conventional transdermal patch system, such as a membrane or a matrix to form the drug delivery element. A conventional transdermal patch system may comprise for example of a backing layer, a drug matrix (e.g. a pellets or particles embedded in a hydrogel, a fat or any suitable polymer) or a drug reservoir (drug in the form of solution or suspension), a membrane (optional) and an adhesive.

The term "matrix" will be understood to include any material where pellets or particles of the composition are formed or embedded. The term "hydrogel" will be understood to include a highly absorbent natural or synthetic polymer, such as HPMC or PVA.

The embedding of pellets or particles of the composition in, for example, a hydrogel, such as a cryogel, creates a pre-saturated gel that is able to administer the active pharmaceutical ingredient co-formedly interspersed within such pellets or particles when the contact surface of the drug delivery element is located, in use, against a patient's skin.

Granules or pellets of the composition may be formed by mixing together the carrier material (e.g. ceramic or geopolymeric material), or precursor(s) thereto, and the active substance, optionally adding a film-forming agent along with, or in, a liquid, such as an aqueous solvent (e.g. water), so providing a wet granulate. Wet granulation techniques are well known to those skilled in the art and include any technique involving the massing of a mix of dry primary powder particles using a granulating fluid, which fluid comprises a volatile, inert solvent, such as water, optionally in the presence of a pelletisation aid material. The product so obtained may further be adapted by:
(I) spheronisation (forcing a wet mass through a sieve to produce pellets);
(II) drying; and/or
(III) (if necessary) hardening by way of heat at temperatures of 20-90° C. for >1 hour, using routine techniques in all cases.

Alternatively, granules or pellets may be formed by forming a wet paste (rather than a granulate) as described above, and directly moulding the paste into the desired shape. The paste is preferably moulded into a polymer mould or into polymer coated metal or ceramic mould (e.g. Teflon coating). After moulding, the paste may be hardened (in a preferably warm and moist environment) to the final desired shape.

If granules or pellets of geopolymer are to be employed, preformed geopolymer may be reacted together further aluminosilicate precursor and aqueous alkaline liquid (e.g. solution), preferably in the presence of a source of silica (as hereinbefore described), also in the presence of the active ingredient and optionally the film-forming agent (or the active ingredient optionally interspersed or dry-mixed with the film-forming agent) as hereinbefore described. Curing may thereafter be performed by allowing the resultant mixture to harden into the required shape, i.e. granules or pellets.

Alternatively, pellets may be manufactured using an appropriate extrusion-spheronization technique. Here, the formed paste (powder and liquid mixture) may be extruded through an orifice. The size of the orifice may be from about 10 μm up to about 30 mm, preferably from about 100 μm to about 1 mm. The formed extrudate may then be placed in a spheronizer, which is typically a vertical hollow cylinder with a horizontal rotating disk located inside. When the disk is spun, the extrudate is broken into uniform lengths and gradually formed into spherical pellets, which may then be left to harden as described hereinbefore.

In embodiments in which the drug delivery element includes pellets of the composition, suitable mean pellet/granule sizes are in the range of about 0.05 mm to about 3.0 mm (e.g. about 2.0 mm, such as about 1.7 mm), and preferably about 0.1 mm (e.g. about 0.2 mm) to about 1.6 mm (e.g. about 1.5 mm), such as about 1.0 mm.

Compositions in the form of small particles of a mean size range of about 0.0001 mm to about 5 mm (e.g. about 0.5 mm), preferably about 0.001 mm to about 0.5 mm (e.g. about 0.05 mm), may also be attached to, or embedded within, an adhesive surface, with or without a backing layer, which is then placed in contact with the skin. In such systems, all, some or none of the small particles may thereafter be in direct contact with the skin upon application. Such small particles may be made by forming a material network with high mechanical strength as described hereinbefore and then crushing (e.g. using a jaw crusher) and/or milling to the desired mean grain size (e.g. using a planetary mill). The formed grains may be essentially angular (i.e. irregular shapes that are essentially not spherical/round).

In the aforementioned embodiments, the composition may further include a pellitisation aid material. A pelletisation aid material may be defined as a material that is capable of controlling the distribution of granulating liquid through the wet powder mass during pelletisation and to modify the rheological properties in the mixture. Suitable pelletisation aid materials include hydroxypropylmethylcellulose (HPMC), hydroxyethylcellulose (HEC) and, preferably, microcrystalline cellulose. If present, the pelletisation aid material is preferably employed in an amount of between 0.5 and 50% by weight based upon the total weight of the tablet formulation. A preferred range is from 1 to 20%, such as from about 2.0 to about 12% (e.g. about 10%) by weight.

In other embodiments, the composition may be moulded during formation into one or more homogeneous layers (e.g. in the form of one or more uniform layers, elements, plates or disks) that may be flat and/or thin defining a drug delivery element in which the active pharmaceutical ingredient is co-formedly dispersed within pores in a solid network of carrier material. Typical dimensions for a single element to be applied to the skin may be in the range of between about 2 cm (e.g. about 5 cm) and about 10 cm by about 2 cm (e.g. about 5 cm) and about 10 cm. Preferred size ranges for single elements are about 5 cm by about 5 cm, such as about 2 cm by about 2 cm, with a thickness of up to about 1 cm, preferably up to about 0.5 cm, such as up to about 0.02 cm. Any of the aforementioned dimensions may be used in combination. Furthermore, multiple elements of the same or different dimensions (e.g. smaller elements of about 1 mm by about 1 mm) may be applied to the skin at the same time to make a "mosaic" pattern of elements.

In such embodiments, the homogeneous layer may be moulded to define a substantially flat contact surface for location, in use, against a patient's skin (in either direct or indirect contact as described hereinbefore).

The term "substantially flat contact surface" will be understood to include a flat contact surface that excludes any pre-formed protrusions and includes only undulations or variations resulting from the moulding process.

In other such embodiments, the homogeneous layer may be moulded to define a contact surface including an array of microscopic protrusions for location, in use, against a patient's skin.

The term "microscopic protrusions" may be provided in the form of any shape that has a base and one or more sloping sides to define (e.g. in the case of more than one side to meet generally centrally at) an apex (i.e. point or ridge, which may be rounded), for example pyramidal protrusions or conical protrusions. Such protrusions may be of about 4 μm to about 700 μm in height and have a width at their lower bases of about 0.1 μm to about 200 μm.

The provision of microscopic protrusions increases the surface area of the contact surface of the drug element available for location against a patient's skin and thereby increases the size (i.e. the contact surface area) of the drug reservoir available for administration via the patient's skin. This improves the transport of the active pharmaceutical ingredient from the drug delivery element via pores in the skin barrier so as to facilitate absorption of the active pharmaceutical ingredient through the skin barrier.

It thus improves the efficiency of the drug delivery element in administering the active pharmaceutical ingredient. The use of such microscopic protrusions is advantageous in the treatment of e.g. chronic disorders in which the ongoing administration of an active pharmaceutical ingredient is required.

Other shapes may be moulded into the contact surface(s) of the drug delivery element in order to increase hydrophobicity or hydrophilicity of at least part of the resultant surface (with or without the employment of surface active molecules). The drug delivery element may thus make use of the so-called "lotus effect", in which the contact angle of certain microscopic protrusion(s) at the surface is high enough (e.g. >90°) to be hydrophobic and/or low enough (e.g. <90°) to be hydrophilic. The moulded structure may thus be designed so that the surface of the drug delivery element is capable of channelling moisture from one part to another, for example any part of the drug delivery element where there are pores comprising active ingredient.

Combinations of the aforementioned microscopic protrusion patterns may be employed in the drug delivery element.

In a further embodiment, the homogeneous layer may be moulded to define an array of micro-needles protruding from the contact surface of the drug delivery element.

The term "micro-needles" will be understood to include sharp protrusions having a length of 4 μm to 700 μm and having a width at their lower bases of 1 μm to 200 μm, which, on placement of a contact surface including an array of micro-needles against a patient's skin, create micron-sized micropores or microchannels in the skin. This facilitates more rapid delivery of active pharmaceutical ingredients, and/or the delivery of larger molecules such as peptides and proteins, for example, which cannot otherwise penetrate the skin barrier.

The size of the micro-needles moulded so as to protrude from the contact surface of the drug delivery element may be varied depending on the nature of the active pharmaceutical ingredient interspersed in the drug delivery element so as to alter the extent of penetration of the needles into the skin barrier.

The homogeneous layer may be moulded to define an array of solid micro-needles, and may further be moulded to define an array of hollow micro-needles. The use of hollow micro-needles allows the accurate delivery of larger molecules of active pharmaceutical ingredient via holes formed in the tips of the micro-needles directly into the micropores or microchannels formed in a patient's skin. Any such holes may have a diameter of between 10 μm and 100 μm.

The use of micro-needles that penetrate a patient's skin is advantageous in the treatment of acute disorders in which a rapid onset of action from an active pharmaceutical ingredient is required. The creation of micropores or microchannels in the patient's skin accelerates the rate at which drug molecules can be absorbed into the patient's bloodstream when compared with the use of a flat contact surface or a contact surface including a plurality of microscopic protrusions.

In embodiments in which the drug delivery element is provided in the form of a homogeneous layer of the composition, so as to define a substantially flat contact surface or so as to define a contact surface including an array of microscopic protrusions or micro-needles protruding therefrom, the homogeneous layer may be formed by filling a production mould with the wet mass of active pharmaceutical ingredient and carrier material or precursor(s) thereto, and forming the curing or bonding step mentioned hereinbefore in situ.

The mould is chosen to define the desired geometry of the resultant homogeneous layer and the wet mass is preferably chemically hardened (i.e. hardens or otherwise cures via chemical reactions) to form the pores in which the active pharmaceutical ingredient (and optionally film-forming agent) is co-formedly dispersed.

Such moulded elements may be formed by mixing together the carrier material (e.g. ceramic or geopolymeric material), or precursor(s) thereto, and the active substance, optionally adding a film-forming agent along with, or in, a liquid, such as an aqueous solvent (e.g. water), so providing a wet paste, and directly moulding the paste into the desired shape. The paste is preferably moulded into a polymer mould or into polymer coated metal or ceramic mould (e.g. Teflon coating). After moulding the paste may be hardened (in a preferably warm and moist environment) to the final desired shape. For example, in the case of geopolymer-based carrier materials, aluminosilicate precursor may be reacted together with aqueous alkaline liquid (e.g. solution), preferably in the presence of a source of silica (as hereinbefore described), also in the presence of the active ingredient (and/or other excipients, such as a film-forming agent) as hereinbefore described and curing thereafter performed by allowing the resultant mixture to harden into the required homogeneous layer shape. Alternatively, preformed geopolymer may be reacted together further aluminosilicate precursor and aqueous alkaline liquid (e.g. solution), in the presence of the active ingredient and optionally a source of silica and curing thereafter performed as described above. In this respect, the mixture may be transferred into moulds and left to set as the homogeneous layer.

In such embodiments, the mould in which the homogeneous layer of composition is formed may form a blister packaging for the drug delivery element, the bottom of the blister forming the negative mould for any microscopic protrusions or micro-needles formed so as to protrude from the contact surface.

Such moulds may be formed by etching (chemical or physical (e.g. by way of a laser)) or known micromechanical techniques, such as soft lithography. Soft lithography is the general name for a number of different nanofabrication techniques in which a master initially is produced on a silicon wafer, for example UV-photolithography. Here, a device layout is printed on a transparency or on a chrome mask, making some areas transparent and others oblique to UV-light. A silicon wafer is then spin-coated with a photo-curable resist, which is exposed to UV-light through the mask. The wafer is then subjected to an etching solution that removes the uncured photoresist to make the master. The master is then used as a mould to cast a negative structure in an elastomer. This elastomer casting is either the end product, or it in turn is used as a mould to make another generation of castings with structures similar to those of the silicon master (see, for example, Madou, *Fundamentals of Microfabrication: The Science of Miniaturization*, $2^{nd}$ ed. (2002), Boca Raton: CRC Press. 723 and Weigl et al, *Advanced Drug Delivery Reviews* (2003) 55, 349-377 for further information).

The active pharmaceutical ingredients employed in the composition included in the drug delivery element preferably include substances from various pharmacological classes, e.g. antibacterial agents, antihistamines and decongestants, anti-inflammatory agents, antiparasitics, antivirals, local anaesthetics, antifungals, amoebicidals or trichomonocidal agents, analgesics, antianxiety agents, anticlotting agents, antiarthritics, antiasthmatics, anticoagulants, anticonvulsants, antidepressants, antidiabetics, antiglaucoma agents, antimalarials, antimicrobials, antineoplastics, antiobesity agents, antipsychotics, antihypertensives, auto-immune disorder agents, anti-impotence agents, anti-Parkinsonism agents, anti-Alzheimer's agents, antipyretics, anticholinergics, anti-ulcer agents, blood-glucose-lowering agents, bronchodilators, central nervous system agents, cardiovascular agents, cognitive enhancers, contraceptives, cholesterol-reducing agents, agents that act against dyslipidermia, cytostatics, diuretics, germicidials, hormonal agents, anti-hormonical agents, hypnotic agents, inotropics, muscle relaxants, muscle contractants, physic energizers, sedatives, sympathomimetics, vasodilators, vasocontrictors, tranquilizers, electrolyte supplements, vitamins, uricosurics, cardiac glycosides, membrane efflux inhibitors, membrane transport protein inhibitors, expectorants, purgatives, contrast materials, radiopharmaceuticals, imaging agents, peptides, enzymes, growth factors, vaccines, mineral trace elements.

The active pharmaceutical ingredients preferably include any that are open to abuse potential, such as those that are useful in the treatment of acute or chronic pain, attention deficit hyperactivity disorders (ADHD), anxiety and sleep disorders, as well as growth hormones (e.g. erythropoietin), anabolic steroids, etc. A full list of potentially abusable substances may be found easily by the skilled person, for example see the active ingredients listed on the following weblink: http://www.deadiversion.usdoj.gov/schedules/alpha/alphabetical.htm.

Non-opioid drug substances that may be specifically mentioned include psychostimulants, such as modafinil, amphetamine, dextroamphetamine, methamphetamine and hydroxyamphethamine and, more preferably, methylfenidate; benzodiazepines, such as bromazepam, camazepam, chlordiazepoxide, clotiazepam, cloxazepam, delorazepam, estazolam, fludiazepam, flurazepam, halazepam, haloxazepam, ketazolam, lormetazepam, medazepam, nimetazepam, nordiazepam, oxazolam, pinazepam, prazepam, temazepam, tetrazepam and, more preferably, alprazolam, clonazepam, diazepam, flunitrazepam, lorazepam, midazolam, nitrazepam, oxazepam and triazolam; and other, non-benzodiazepine sedatives (e.g. short-acting hypnotics), such as zaleplon, zolpidem, zopiclone and eszopiclone.

Preferred pharmaceutically-active ingredients that may be employed in the composition include opioid analgesics. The term "opioid analgesic" will be understood by the skilled person to include any substance, whether naturally-occurring or synthetic, with opioid or morphine-like properties and/or which binds to opioid receptors, particularly the p-opioid receptor, having at least partial agonist activity, thereby capable of producing an analgesic effect. The problems of potential formulation tampering and drug extraction by drug addicts are particularly prominent with opioids.

Opioid analgesics that may be mentioned include opium derivatives and the opiates, including the naturally-occurring phenanthrenes in opium (such as morphine, codeine, thebaine and Diels-Alder adducts thereof) and semisynthetic derivatives of the opium compounds (such as diamorphine, hydromorphone, oxymorphone, hydrocodone, oxycodone, etorphine, nicomorphine, hydrocodeine, dihydrocodeine, metopon, normorphine and N-(2-phenylethyl)normorphine). Other opioid analgesics that may be mentioned include fully synthetic compounds with opioid or morphine-like properties, including morphinan derivatives (such as racemorphan, levorphanol, dextromethorphan, levallorphan, cyclorphan, butorphanol and nalbufine); benzomorphan derivatives (such as cyclazocine, pentazocine and phenazocine); phenylpiperidines (such as pethidine (meperidine), fentanyl, alfentanil, sufentanil, remifentanil, ketobemidone, carfentanyl, anileridine, piminodine, ethoheptazine, alphaprodine, betaprodine, 1-methyl-4-phenyl-1,2,3,6-tetrahydropyridine (MPTP), diphenoxylate and loperamide), phenylheptamines or "open chain" compounds (such as methadone, isomethadone, propoxyphene and levomethadyl acetate hydrochloride (LAAM)); diphenylpropylamine derivatives (such as dextromoramide, piritramide, bezitramide and dextropropoxyphene); mixed agonists/antagonists (such as buprenorphine, nalorphine and oxilorphan) and other opioids (such as tilidine, tramadol and dezocine). Further opioid analgesics that may be mentioned include allylprodine, benzylmorphine, clonitazene, desomorphine, diampromide, dihydromorphine, dimenoxadol, dimepheptanol, dimethylfthiambutene, dioxaphetyl butyrate, dipipanone, eptazocine, ethylmethylthiambutene, ethylmorphine, etonitazene, hydroxypethidine, levophenacylmorphan, lofentanil, meptazinol, metazocine, myrophine, narceine, norpipanone, papvretum, phenadoxone, phenomorphan, phenoperidine and propiram.

More preferred opioid analgesics include buprenorphine, alfentanil, sufentanil, remifentanil and, particularly, fentanyl.

Active ingredients listed above may also be formulated in the composition in any specific combination.

In the case of drug delivery devices comprising opioid analgesics, in order to further improve abuse-deterrent properties, an opioid antagonist with limited or no transdermal absorption may be included in the composition together with the opioid. Any attempt to tamper with the formulation for subsequent injection, will also release the antagonist and therefore potentially prevent the desired abuse-generated pharmacological effect. Examples of opioid antagonists and partial opioid antagonists include naloxone, naltrexone, nalorphine and cyclazocine.

Active pharmaceutical ingredients may further be employed in salt form or any other suitable form, such as e.g. a complex, solvate or prodrug thereof, or in any physical form such as, e.g., in an amorphous state, as crystalline or part-crystalline material, as co-crystals, or in a polymorphous form or, if relevant, in any stereoisomeric form including any enantiomeric, diastereomeric or racemic form, or a combination of any of the above.

Pharmaceutically-acceptable salts of active ingredients that may be mentioned include acid addition salts and base addition salts. Such salts may be formed by conventional means, for example by reaction of a free acid or a free base form of an active ingredient with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of active ingredient in the form of a salt with another counter-ion, for example using a suitable ion exchange resin.

Examples of pharmaceutically acceptable addition salts include those derived from mineral acids, such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

The drug delivery element of the transdermal drug administration device contains a pharmacologically effective amount of the active ingredient. By "pharmacologically effective amount", we refer to an amount of active ingredient, which is capable of conferring a desired therapeutic effect on a treated patient (which may be a human or animal (e.g. mammalian) patient), whether administered alone or in combination with another active ingredient. Such an effect may be objective (i.e. measurable by some test or marker) or subjective (i.e. the subject gives an indication of, or feels, an effect).

Preferably the drug delivery element may be adapted (for example as described herein) to provide a sufficient dose of drug over the dosing interval to produce a desired therapeutic effect.

The amounts of active ingredients that may be employed in the drug delivery element may thus be determined by the physician, or the skilled person, in relation to what will be most suitable for an individual patient. This is likely to vary with the type and severity of the condition that is to be treated, as well as the age, weight, sex, renal function, hepatic function and response of the particular patient to be treated.

When the drug delivery element includes opioid analgesics, appropriate pharmacologically effective amounts of such opioid analgesic compounds include those that are capable of producing (e.g. sustained) relief of pain when administered.

Drug delivery elements including opioid analgesics are useful in the treatment of pain, particularly severe and/or chronic pain. According to a further aspect of the invention there is provided a method of treatment of pain which comprises locating a contact surface of such a drug delivery element of a transdermal drug administration device according to the invention against the skin of a patient suffering from, or susceptible to, such a condition.

For the avoidance of doubt, by "treatment" we include the therapeutic (including curative) treatment, as well as the symptomatic treatment, the prophylaxis, or the diagnosis, of the condition.

Transdermal drug administration devices of the invention possess the advantage of the avoidance and/or reduction of the risk of either dose dumping (i.e. the involuntary release), or equally importantly the deliberate ex vivo extraction, of the majority (e.g. greater than about 50%, such as about 60%, for example about 70% and in particular about 80%) of the dose of the active ingredient(s) that is initially within the composition included in the drug delivery element, within a timeframe that is likely to give rise to undesirable consequences, such as adverse pharmacological effects, or the potential for abuse of that active ingredient (for example when such release is deliberately effected ex vivo by an individual).

Transdermal drug administration devices of the invention have the advantage that the composition included in the drug delivery element provides sustained release properties with minimal risk for severe/lethal side effects (i.e. reduction of dose dumping and/or abuse potential when the active ingredient to be employed is abusable, such as an opioid, a benzodiazepine, etc.). The composition may provide protection against intentional mechanical breakdown, e.g. by traditional methods such as crushing, pestle and mortar, hammering etc by having a high compressive strength level at the micro-level. This protection may be provided by the composition as such, and especially when those compositions are employed in conjunction with a carrier or filler that also possesses high mechanical strength.

Transdermal drug administration devices of the invention may also have the advantage that the composition included in the drug delivery element may be prepared using established pharmaceutical processing methods and may employ materials that are approved for use in foods or pharmaceuticals or of like regulatory status.

Transdermal drug administration devices of the invention may also have the advantage that the composition included in the drug delivery element may be more efficacious than, be less toxic than, be longer acting than, be more potent than, produce fewer side effects than, be more easily absorbed than, and/or have a better pharmacokinetic profile than, and/or have other useful pharmacological, physical, or chemical properties over, pharmaceutical compositions known in the prior art, whether for use in the treatment of pain or otherwise.

Wherever the word "about" is employed herein in the context of dimensions (e.g. values, temperatures, pressures (exerted forces), relative humidities, sizes and weights, particle or grain sizes, pore sizes, timeframes etc.), amounts (e.g. relative amounts (e.g. numbers or percentages) of particles, individual constituents in a composition or a component of a composition and absolute amounts, such as doses of active ingredients, numbers of particles, etc), deviations (from constants, degrees of degradation, etc) it will be appreciated that such variables are approximate and as such may vary by ±10%, for example ±5% and preferably ±2% (e.g. ±1%) from the numbers specified herein.

The invention is illustrated by the following examples in which.

EXAMPLE 1

Zolpidem-Containing Transdermal Drug Delivery Element

Figure 1:
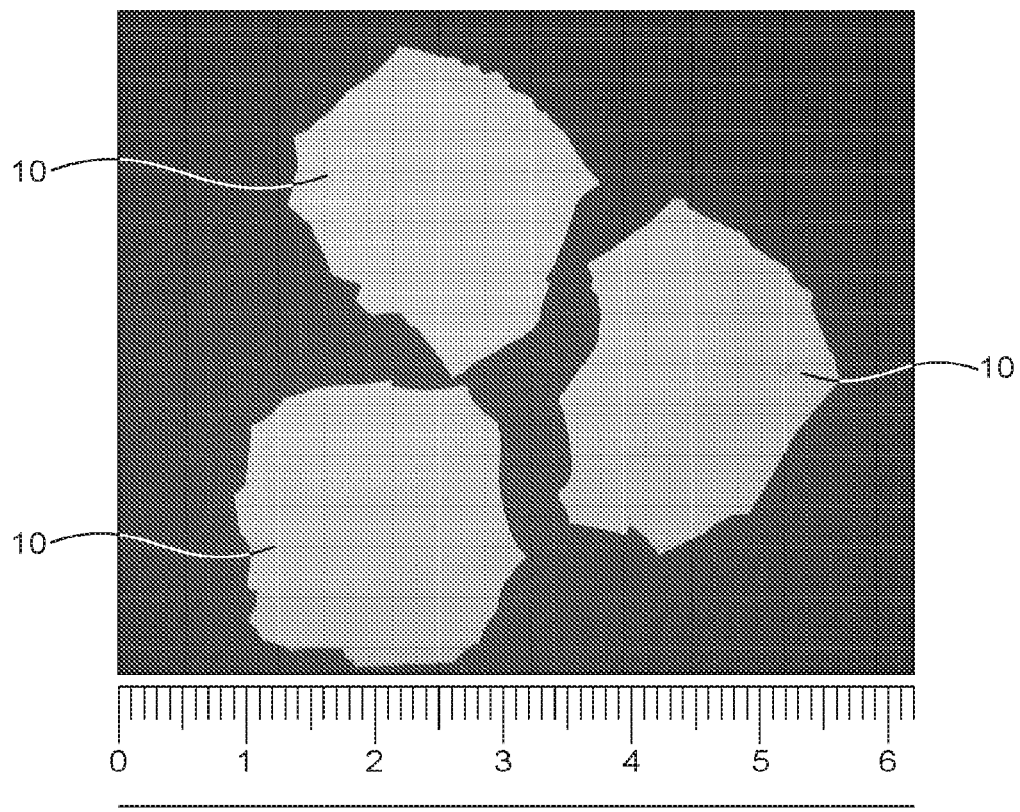
FIGS. 1 and 2 show drug delivery elements of transdermal drug delivery elements made from metakaolin and zolpidem tartrate, and employing sodium silicate solution and water as the granulation liquid. The scale in FIG. 1 is a centimetre scale.
Figure 2:
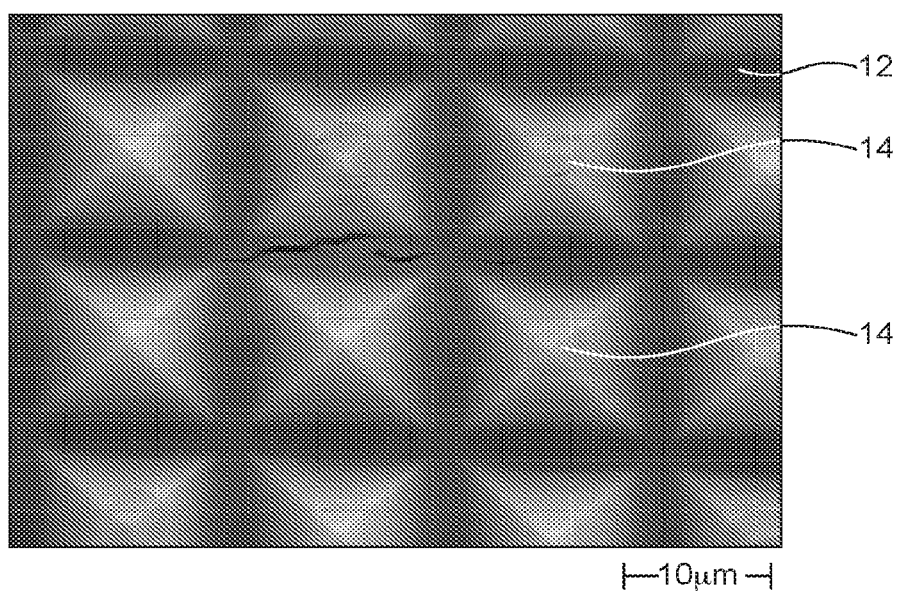

Drug delivery elements 10 of transdermal drug administration devices (not shown) are shown in FIGS. 1 and 2.

Each drug delivery element 10 is a homogeneous layer moulded to define a contact surface 12 including a plurality of microscopic projections 14. The projections 14 are pyramidal in shape, having a height of 4 μm and a width at their base of 10 μm.

The drug delivery element 10 shown in FIGS. 1 and 2 was formed in accordance with the following method.

Kaolin was heated at 800° C. for 2 hours in order to form metakaolin. 4 g of the metakaolin was mixed with 0.12 g of zolpidem tartrate as the active pharmaceutical ingredient, by hand, in a mortar. 5 g of sodium silicate solution and 1 g of water were added to the mixture so as to form a wet mass.

The wet mass was moulded in a plexiglass disc on the bottom of which a pyramidal pattern had been produced using a soft lithography technique, so as to produce the pyramidal projections shown in FIG. 2. A chemical reaction between the sodium silicate solution and the metakaolin resulted in hardening of the wet mass so as to form a solid, continuous network of metakaolin, the network further defining a plurality of pores in which the zolpidem tartrate is dispersed.

The in vitro release profile of the active pharmaceutical ingredient, zolpidem tartrate, of the drug delivery element 10 was measured using the United States Pharmacopoeia <711> (USP) dissolution paddle method. The paddle rotation rate was 50 rpm and 200 mL of phosphate buffer having a pH of 6.8 was used. Samples were withdrawn after 1, 2, 3, 4, 6 and 72 hours and the amount of active pharmaceutical ingredient was determined uysing High Performance Liquid Chromatography (HPLC). The release profile obtained is shown in FIG. 3.

The release profile rate was also evaluated using a dish rag/cloth (wettex) method. In this evaluation, 400 μL of phosphate buffer was placed on a piece of wettex material measuring 3 cm×3 cm. A para film and a metal plate were placed over the wettex material. The drug was extracted from the wettex material after 6 and 24 hours and the amount of active pharmaceutical ingredient was determined uysing High Performance Liquid Chromatography (HPLC). The release profile obtained is shown in FIG. 4.

Figure 3:
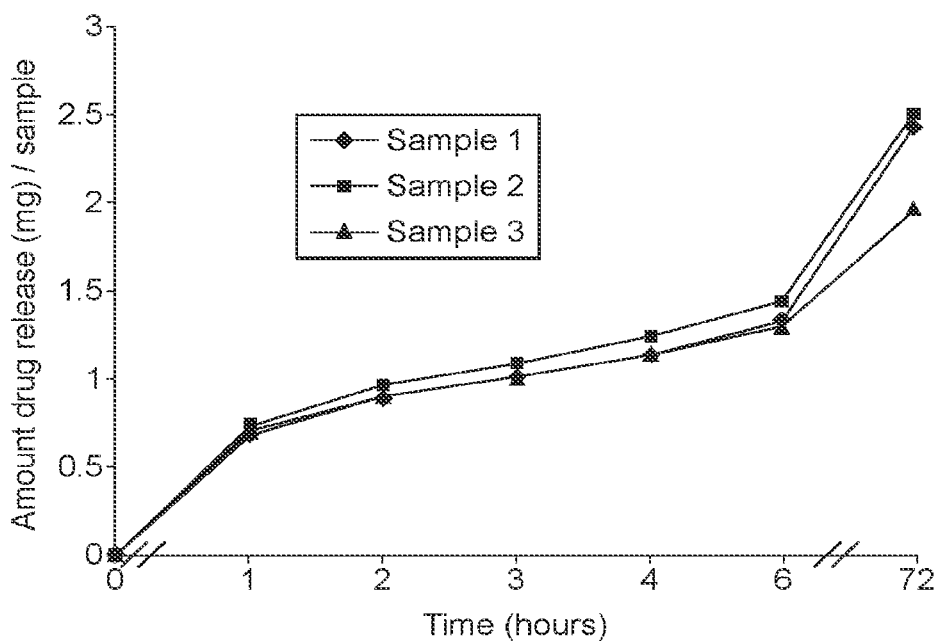
FIGS. 3 and 4 shows the release profile of zolpidem tartrate in phosphate buffer (pH 6.8) from the drug delivery elements shown in FIGS. 1 and 2.
Figure 4:
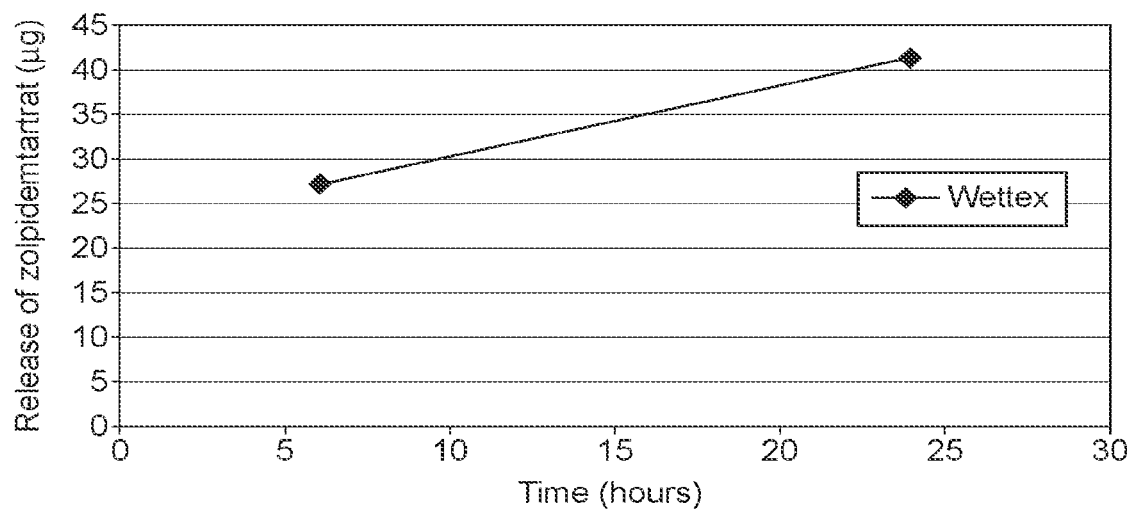

On reviewing the release profiles shown in FIGS. 3 and 4, it can be seen that both dissolution methods gave relatively slow release of the drug. The use of a relatively large volume (200 mL) of buffer solution in the conventional USP dissolution method resulted in a higher total amount of the released drug, which approached the drug load.

In other embodiments a film forming agent, such as Kollicoat MAE 30 DP, may be mixed with the metakaolin and zolpidem tartrate prior to the addition of the sodium silicate solution and water so as to decrease the dissolution rate of the active pharmaceutical ingredient from the resultant homogeneous layer of composition in different media such as, for example, low pH, ethanol and hot water.

EXAMPLE 2

Fentanyl-Containing Pellets for Transdermal Drug Delivery

Fentanyl base (MacFarlan and Smith, Edinburgh, UK), Eudragit L100-55 (Evonik industries, Germany), kaolin ($Al_2Si_2O_5(OH)_4$), fumed silica ($SiO_2$, 7 nm particle size) and reagent grade sodium hydroxide (NaOH) were purchased from Sigma-Aldrich (Stockholm, Sweden).

Metakaolin was prepared by heating the kaolin at 800° C. for two hours. Waterglass was prepared by dissolving 24.398 g of NaOH and 26.306 g of $SiO_2$ into 50 mL of distilled water.

Dry materials (metakaolin, Eudragit and fentanyl) were mixed and then the waterglass added in a glass mortar until a homogeneous paste was formed. The paste was applied to a Teflon mould with holes to make cylindrical pellets (1.5×1.5 mm or 1×1 mm, diameter×height). The moulds were placed in an oven set at 37° C. oven (100% relative humidity (RH)) for 48 hours. After the synthesis was complete, the samples were air-dried for one day and released from the moulds.

Two differently-sized sets of pellets were prepared, starting with:
(a) 8 g of metakaolin, 1.0019 g of Eudragit, 0.2401 g of fentanyl and 14.04 g of the waterglass (providing 11.067 mg of fentanyl per gram of 1×1 mm pellets); and
(b) 4 g of metakaolin, 0.50068 g of Eudragit, 0.12033 g of fentanyl and 6.03 g of the waterglass (providing 11.945 mg of fentanyl per gram of 1.5×1.5 mm pellets).

Zolpidem-containing pellets were also prepared using essentially the same process (3 sets of 1.5×1.5 mm pellets containing 1.862 mg, 0.878 mg and 0.158 mg, respectively, of zolpidem in 150 mg of pellets, and one set of 1×1 mm pellets containing 1.862 mg of zolpidem in 150 mg of pellets).

The invention claimed is:

1. An abuse-resistant transdermal drug administration device comprising a drug delivery element defining a contact surface for location, in use, against a patient's skin, the drug delivery element including a sustained-release pharmaceutical composition comprising one or more active pharmaceutical ingredients co-formedly interspersed within pores of a solid, continuous network comprising a carrier material and possessing a mechanical strength sufficient to maintain the overall integrity of the network when a force of at least about 1 kg-force/cm$^2$ (9 newtons/cm$^2$) is applied thereto, wherein said one or more active pharmaceutical ingredients includes a substance that is open to abuse potential, and wherein said carrier material is based on one or more chemically bonded ceramics.

2. A transdermal drug administration device according to claim 1 wherein the carrier material is based on one or more chemically bonded ceramics selected from the group consisting of calcium phosphates, calcium sulphates, calcium carbonates, calcium silicates and calcium aluminates.

3. A transdermal drug administration device according to claim 2 wherein the carrier material is based on one or more chemically bonded ceramics selected from the group consisting of calcium phosphates, calcium sulphates, calcium silicates and calcium aluminates.

4. A transdermal drug administration device according to claim 2 wherein the calcium silicate is dicalcium silicate or tricalcium silicate.

5. A transdermal drug administration device according to claim 1 wherein the drug delivery element is formed from pellets of the composition embedded in a patch matrix.

6. A transdermal drug administration device according to claim 1 wherein the drug delivery element is formed from particles of the composition embedded in a patch matrix.

7. A transdermal drug administration device according to claim 5 wherein the composition further includes a pelletisation aid material.

8. A transdermal drug administration device according to claim 7 wherein the pelletisation aid material is microcrystalline cellulose.

9. A transdermal drug administration device according to claim 1 wherein the drug delivery element is formed from a homogeneous layer of the composition.

10. A transdermal drug administration device according to claim 9 wherein the contact surface of the drug delivery element is substantially flat.

11. A transdermal drug administration device according to claim 9 wherein the contact surface of the drug delivery element is moulded to define an array of microscopic protrusions.

12. A transdermal drug administration device according to claim 11 wherein the contact surface of the drug delivery element is moulded to define an array of microscopic pyramidal protrusions.

13. A transdermal drug administration device according to claim 9 wherein the contact surface of the drug delivery element is moulded to define an array of micro-needles.

14. A transdermal drug administration device according to claim 1 wherein the composition further includes a film forming agent co-formedly interspersed within the pores.

15. A transdermal drug administration device according to claim 14 wherein the film forming agent is an enteric coating material.

16. A transdermal drug administration device according to claim 15 wherein the film forming agent is a copolymer derived from methacrylic acid and ethyl acrylate or a neutral methacrylic polymer with acid or alkaline groups.

17. A transdermal drug administration device according to claim 1 wherein the one or more active pharmaceutical ingredients includes a substance that is useful in the treatment of a disease or disorder selected from the group consisting of acute or chronic pain, attention deficit hyperactivity disorders (ADHD), anxiety and sleep disorders, or wherein the one or more active pharmaceutical ingredients includes a growth hormone or an anabolic steroid.

18. A transdermal drug administration device according to claim 17 wherein the one or more active pharmaceutical ingredients includes an opioid analgesic.

19. A transdermal drug administration device according to claim 17 wherein the opioid analgesic is a morphinan derivative, a benzomorphan derivative, a phenylpiperidine, a phenylheptamine, an open chain compound, a diphenylpropylamine derivative, a mixed agonist/antagonist or another synthetic opioid.

20. A transdermal drug administration device according to claim 19 wherein the opioid analgesic is selected from morphine, codeine, thebaine or a Diels-Alder adduct thereof, diamorphine, hydromorphone, oxymorphone, hydrocodone, oxycodone, etorphine, nicomorphine, hydrocodeine, dihydrocodeine, metopon, normorphine, N-(2-phenylethyl)normorphine, racemorphan, levorphanol, dextromethorphan, levallorphan, cyclorphan, butorphanol, nalbufine, cyclazocine, pentazocine, phenazocine, pethidine (meperidine), fentanyl, alfentanil, sufentanil, remifentanil, ketobemidone, carfentanyl, anileridine, piminodine, ethoheptazine, alphaprodine, betaprodine, 1-methyl-4-phenyl-1,2,3,6-tetrahydropyridine, diphenoxylate, loperamide, methadone, isomethadone, propoxyphene, levomethadyl acetate hydrochloride, dextromoramide, piritramide, bezitramide, dextropropoxyphene, buprenorphine, nalorphine, oxilorphan, tilidine, tramadol, allylprodine, benzylmorphine, clonitazene, desomorphine, diampromide, dihydromorphine, dimenoxadol, dimepheptanol, dimethylthiambutene, dioxaphetyl butyrate, dipipanone, eptazocine, ethylmethylthiambutene, ethylmorphine, etonitazene, hydroxypethidine, levophenacylmorphan, lofentanil, meptazinol, metazocine, myrophine, narceine, norpipanone, papvretum, phenadoxone, phenomorphan, phenoperidine, propiram and dezocine.

21. A transdermal drug administration device according to claim 20 wherein the opioid analgesic is selected from the group consisting of buprenorphine, alfentanil, sufentanil, remifentanil, fentanyl, and pharmaceutically-acceptable salts thereof.

22. A transdermal drug administration device according to claim 21 wherein the opioid analgesic is fentanyl or a pharmaceutically-acceptable salt thereof.

23. A transdermal drug administration device according to claim 13, wherein the one or more active pharmaceutical ingredients is a peptide or a protein.

24. A method of treatment of pain, which method comprises locating a contact surface of a drug delivery element of a transdermal drug administration device according to claim 18 against the skin of a patient suffering from, or susceptible to, such a condition.

25. A transdermal drug administration device according to claim 21 wherein the opioid analgesic is buprenorphine or a pharmaceutically-acceptable salt thereof.

* * * * *